United States Patent [19]

McFarland

[11] Patent Number: 4,942,774
[45] Date of Patent: Jul. 24, 1990

[54] ANISOKINETIC SHROUDED AEROSOL SAMPLING PROBE

[75] Inventor: Andrew R. McFarland, College Station, Tex.

[73] Assignee: The Texas A & M University System, College Station, Tex.

[21] Appl. No.: 325,987

[22] Filed: Mar. 20, 1989

[51] Int. Cl.⁵ .............................................. G01N 1/00
[52] U.S. Cl. ............................. 73/864.81; 73/863.51
[58] Field of Search .................. 73/28, 863.21, 863.41, 73/863.43, 863.51, 863.58, 864.73, 864.81; 55/270

[56] References Cited

U.S. PATENT DOCUMENTS

| | | | |
|---|---|---|---|
| 3,106,843 | 10/1963 | Luxl | 73/863.12 |
| 3,289,481 | 12/1966 | Barnes | 73/863.21 |
| 3,559,491 | 2/1971 | Thoen | 73/863.24 |
| 3,954,428 | 5/1976 | Marple et al. | 55/270 |
| 3,983,743 | 10/1976 | Olin et al. | 73/28 |
| 4,091,835 | 5/1978 | Frampton | 73/863.51 |
| 4,140,005 | 2/1979 | Kittelson | 55/270 |
| 4,221,130 | 9/1980 | Burrows | 73/863.58 |
| 4,353,260 | 10/1982 | Rounds | 73/863.41 |
| 4,796,475 | 1/1989 | Marpel | 73/863.22 |

OTHER PUBLICATIONS

"An Aircraft Impactor for Determining the Size Distribution of Tropospheric Aerosols", by W. L. Torgeson & S. C. Stern, *Journal of Applied Meterology,* 5:205–210, Apr. 1966.

*Primary Examiner*—Robert Raevis
*Attorney, Agent, or Firm*—Arnold, White & Durkee

[57] ABSTRACT

This invention relates to an aerosol sampling probe and method used for the collection of samples from moving fluid streams. A shroud surrounds the probe which enables the collection of more representative concentrations of aerosol particles in the fluid stream in many sampling applications.

10 Claims, 2 Drawing Sheets

ANISOKINETIC SHROUDED AEROSOL SAMPLING PROBE

BACKGROUND OF THE INVENTION

For a variety of reasons, it is often necessary to measure the amount of aerosol particulate matter in a moving fluid stream. Four examples of such measurement requirements are given below. These examples are merely illustrations.

The concentration of particulate matter in industrial smokestacks is frequently measured with apparatus which separates aerosol particles that are not inhalable into the thoracic region of the human respiratory system from those that are. The latter category of particles is associated with sizes less than or equal to 10 micrometers aerodynamic diameter and is referred to as PM-10 aerosol. Fractionation of the aerosol size distribution is accomplished by drawing stack gas into a probe and then through a device such as a cyclone separator. To maintain a consistency of fractionation characteristics, the air flow rate through the separator must be held constant in spite of needs for varying the inlet velocity through the probe in order to satisfy isokinetic requirements. PM-10 particulate matter which passes through the stack is measured to determine compliance with federal, state and local regulations.

An example of continuously monitoring a moving gas stream for particulate matter is that associated with a ventilation system for a clean room. Such rooms are used for assembling precision electronic and mechanical devices and for medical and biological purposes. The air to be supplied to a clean room is generally filtered mechanically. It is important that the air is then continuously monitored and analyzed for concentrations of airborne particles of certain sizes to insure that the level of contamination in the room is compatible with usage requirements.

The useful life of gas turbine engines is dependent on the amount of atmospheric dust drawn in with the combustion air. In the case of small engines as in helicopters, the cost of monitoring the dust in the inlet air is not justified. In large industrial applications, a defective filter can destroy a multimillion dollar engine. It is important to periodically or continuously monitor the inlet air for particulate contamination.

A fourth instance of the importance of measuring particulate matter in a gas stream is in the field of processing and handling of nuclear materials waste. In one application, nuclear waste is to be sealed in drums and stored in an underground salt mine. During the time period (approximately 25 years) that the waste will be received at the mine, ventilation air is drawn down mine shafts and exhausted back to the surface through a central shaft. If radioactivity is inadvertently released, continuous air sampling devices would need to activate alarms and ventilation air controls to protect workers and prevent release of radioactive particles to the environment.

The known method of taking samples from a moving fluid stream is to introduce a probe into that stream and withdraw a fluid sample. The sample is then analyzed to determine the characteristics of particulate matter. The physical presence of the probe in a moving gas stream disturbs the gas flow in the vicinity of the probe. As the gas is forced past or into the probe, the normally parallel flow paths of the gas are curved or distorted. Particulate matter carried along by the gas stream is subjected to inertial forces which tend to cause the particles to continue in a straight line. Because these inertial forces are directly proportional to the particle mass, larger and/or more dense particles tend to deviate from the curving gas flow less than smaller and/or less dense particles. This could cause a sample to have a disproportionately large or small particulate concentration relative to the stream being sampled depending on how the flow is disturbed and what size and type of particles are in that stream.

Previous attempts to solve this problem have been by the use of isokinetic probes. An isokinetic probe is operated so that the fluid velocity (V) inside the mouth of the probe is the same as the temporal mean free stream velocity (U) upstream of the probe. The term isokinetic is derived from the fact that the specific kinetic energy of the free stream is the same as that of the sample entering the probe. Isokinetic sampling is distinguished from sub-isokinetic sampling, in which the velocity of the sample in the probe (V) is less than the mean velocity of the free stream (U) and supra-isokinetic sampling in which V is greater than U. Isokinetic operation (V=U) causes the least amount of flow disturbance.

However, continuous isokinetic operation of a probe is difficult to obtain in actual applications because a change in the velocity of the free stream must be accompanied by a change in velocity of the probe sample. It is apparent that for continuous monitoring a complicated sensing and control system is required to maintain the fluid velocity in the probe the same as that of a varying free stream. Also, if the sample is being fed to a fractionator for analysis, that fractionator will require a constant flow rate. If the flow rate must be maintained constant to the fractionator but varied through the probe, an even more complex control or sampling system is required.

An additional problem of operating an isokinetic probe is that of wall losses due to either turbulent deposition or anisokinetic effects. In the case of turbulent deposition, large diameter probes and low velocities are preferred. The larger the probe diameter, the smaller the ratio of particle stopping distance to probe diameter and less the chance for material to be driven from the sampled stream to the wall. Lower velocities are preferred because the inertial effects are reduced as velocity V is decreased. However, in isokinetic sampling the velocity V is fixed by U and the probe diameter is fixed by the combination of flow rate requirements and the velocity V.

SUMMARY OF THE INVENTION

The present invention overcomes many of these prior art drawbacks and disadvantages through a gas sampling probe physically similar to those known in the art but which is concentrically located inside a shroud open to flow. The shroud and the probe are oriented in the flowing fluid stream to be sampled such that the shroud decelerates the fluid stream in the vicinity of the probe before it reaches the probe mouth. By decelerating the free stream flow, the shroud allows a larger diameter probe than could otherwise be used for a given flow rate requirement with an isokinetic probe. This larger diameter reduces wall losses and anisokinetic effects at the probe inlet. There is less deviation of the flow and therefore a lesser percentage of particles which enter the probe at an angle and strike the interior walls. This results in more accurate sampling of the particulate concentration. The shroud also causes the anisokinetic flow disturbances due to a foreign object in the flow stream to be concentrated at the entry end of the shroud rather than at the mouth of the probe where it would adversely affect the sampling process. Finally because the shroud is larger in diameter than the probe, because a larger probe may be used when the probe is shrouded, and because the anisokinetic effects of flow disturbance are approximately inversely proportional to the cube of the diameter of the object causing the disturbance, the overall anisokinetic effects are substantially lessened.

The cumulative result of the three factors above is that a properly designed shrouded probe will obtain accurate samples without the necessity that it be operated isokinetically with respect to the stream being sampled. Since isokinetic operation of a sample probe is extremely difficult to achieve and maintain in continuous monitoring, the ability to obtain accurate samples without the need for isokinetic operation is a major achievement in the art of aerosol sampling.

These and other advantages and meritorious features will be more fully appreciated by those skilled in the art from the following description of the invention.

DETAILED DESCRIPTION OF THE INVENTION

Figure 5A:
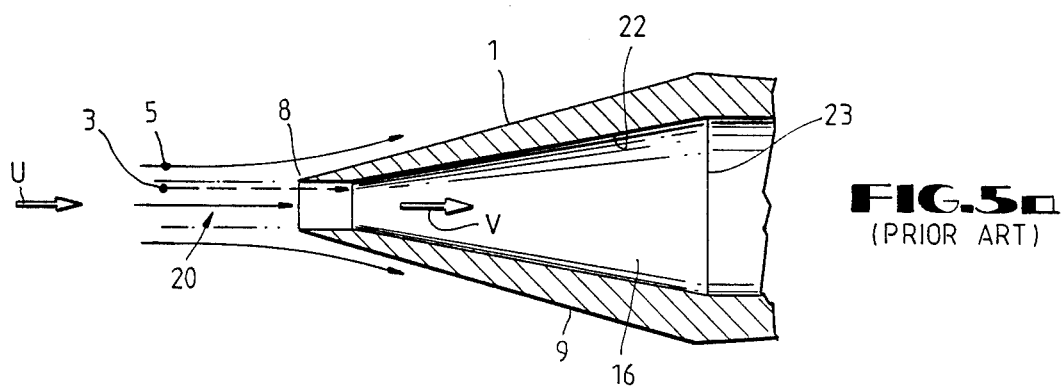
FIG. 5a is a schematic cross sectional view of the probe inlet of FIG. 4 with gas streamlines and particle paths indicated to show how the probe would operate isokinetically without a shroud.
Figure 5B:
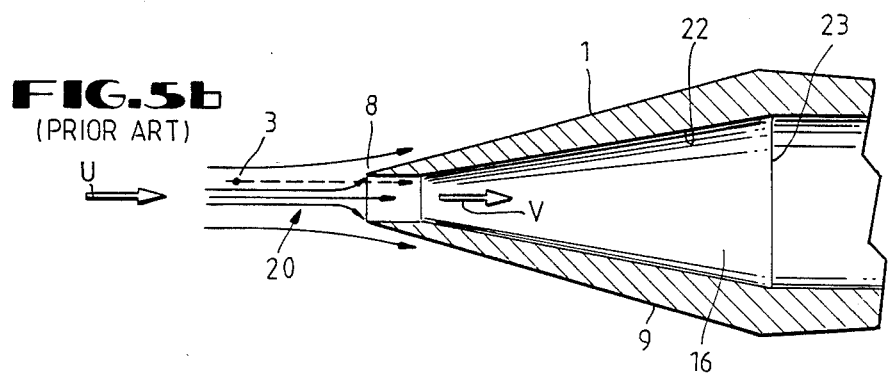
FIG. 5b is a schematic cross sectional view of the probe inlet of FIG. 4 with gas streamlines and particle paths indicated to show how the probe would operate subisokinetically without a shroud.
Figure 5C:
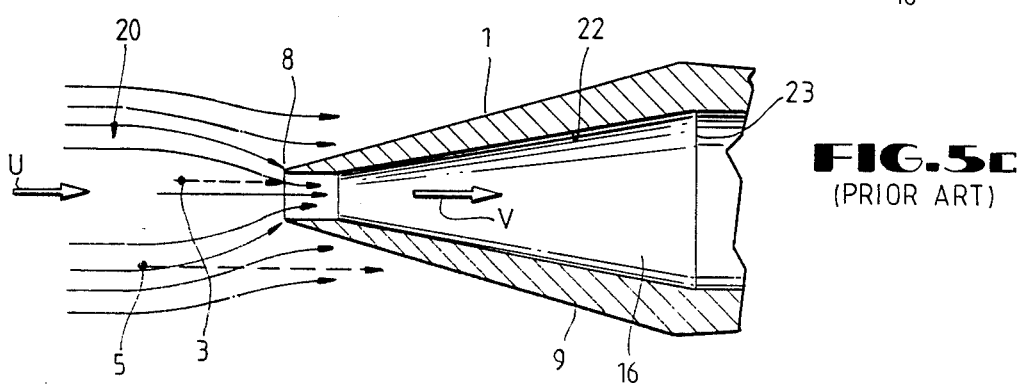
FIG. 5c is a schematic cross sectional view of the probe inlet of FIG. 4 with gas streamlines and particle paths indicated to show how the probe would operate supra-isokinetically without a shroud.

FIGS. 5a, 5b and 5c schematically depict in cross section how an unshrouded probe 1 operates in the three possible flow conditions which might exist. In the figures referred to herein, entrained particles are not shown, but are only schematically represented. All particles that are upstream of the probe and which would enter the probe mouth if they traveled in a straight path parallel to and in the direction of the free stream mean velocity vector U are represented by a single particle 3. All particles that are upstream of the probe and which would not enter the probe mouth if they traveled in a straight path parallel to and in the direction of the free stream mean velocity vector U are represented by a single particle 5.

FIG. 5a shows a probe operating isokinetically without a shroud. The velocity U of the free stream 20 is equal to the velocity V of the fluid just after entering the probe 1. This isokinetic operation causes the least disturbance of the flow at the probe mouth 8. The gas flows in relatively straight streamlines in the free stream 20 and continues in relatively straight lines into the mouth 8 of the probe 1. Since the gas flow is straight, aerosol particles 3 directly upstream of the probe mouth 8 carried by the gas flow into the probe 1 in straight lines and in essentially the same concentration as that of the free stream 20. Particles 5 which are not directly upstream of the probe mouth 8 do not enter the probe 1. The concentration of particulate matter in the gas sample taken into the probe 1 is the same as the concentration in the free stream. As discussed previously, though, the concentration of aerosol particles downstream of cross section 23 may not be the same as free stream particle concentration in the free stream 20 due to internal wall losses in the probe.

Now, by referring to FIG. 5b, we see the same probe 1 (still without a shroud) operating sub-isokinetically, i.e., the velocity V just after the fluid enters the probe mouth 8 is less than the free stream fluid velocity U. Since V is less than U, the amount of fluid that can enter the probe 1 is reduced relative to FIG. 5a. Some of the fluid that would enter a probe operated isokinetically is now deflected around the probe 1 causing the streamlines in the vicinity of the probe mouth 8 to follow a curved path. The inertia of particles 3 immediately upstream of the probe mouth 8 causes them to resist following the curving flow path of the fluid and these particles 3 have a tendency to continue into the probe 1. This, in turn, causes enrichment of the particulate matter in the fluid sample entering the probe 1 and results in inaccurate sampling. The greater the difference between U and V, the greater the deflection of fluid at the probe mouth 8 and the greater the enrichment effect.

Now, by referring to FIG. 5c, we can see the effect of operating the same unshrouded probe 1 supra-isokinetically. In this case, the fluid velocity V just inside the probe 1 is greater than the free stream velocity U. Fluid is drawn into the probe mouth 8 from the area adjacent to the probe mouth 8 causing the fluid streamlines to curve in toward the probe mouth 8. As with a sub-isokinetic probe, any particles 3 and 5 entrained in the fluid stream will tend to continue in a straight line due to their inertia. In this case, however, that inertial effect causes a depletion of particle concentration entering the probe mouth. The fluid near the mouth 8 is drawn in and follows curved streamlines but associated particles 5 continue on past the probe rather than follow the curved streamlines of the fluid. The fluid sample in the probe 1 will have a lower concentration of aerosol particles than the surrounding free stream.

Figure 1:
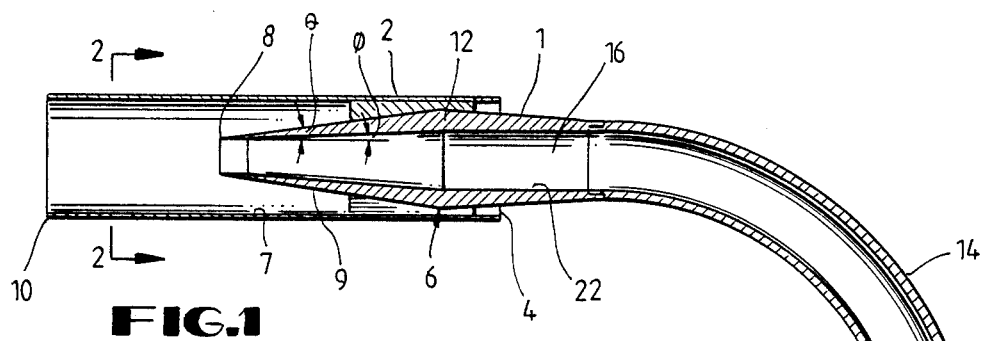
FIG. 1 is a cross sectional view of a shrouded gas sampling probe.
Figure 2:
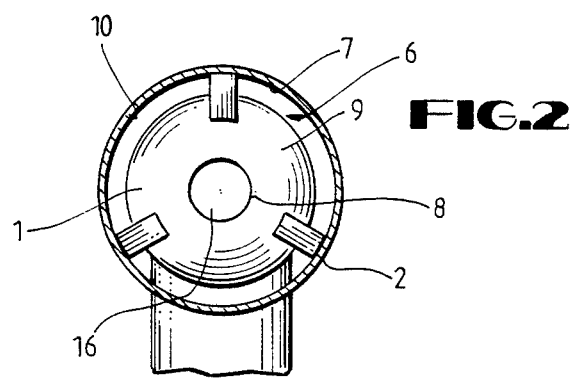
FIG. 2 is a sectional view of the shrouded probe of FIG. 1 as it would appear viewed from position ZZ.
Figure 4:
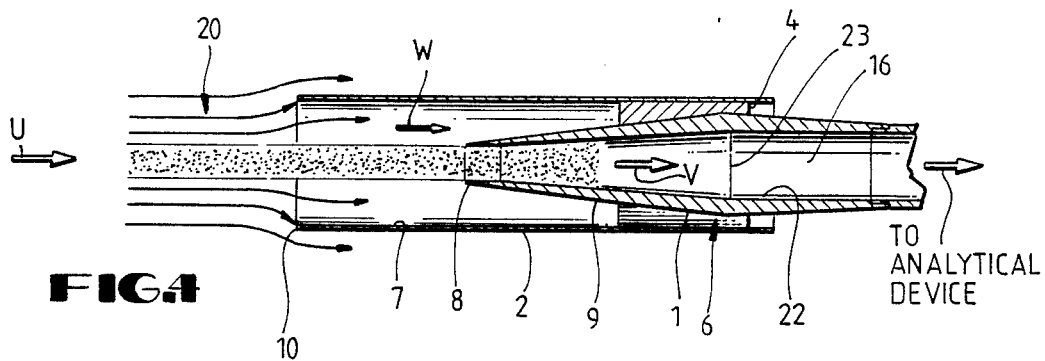
FIG. 4 is a schematic cross sectional view of a shrouded probe with gas streamlines and particle paths indicated to show how the probe operates anisokinetically or isokinetically.

FIGS. 1, 2 and 4 illustrate how the present invention operates to solve the problems of varying free stream velocity illustrated by FIGS. 5a, 5b and 5c. Referring to FIGS. 1, 2 and 4 together, it can be seen that the invention consists of a hollow cylindrical probe 1 which tapers externally from a feathered entry mouth 8 to a relatively thick cross section 12. The external half angle of taper $\theta$, in probes tested by the inventor, varied from 7 degrees to 12 degrees. The internal half angle $\phi$ is greater than 0 but less than $\theta$ so that both the diameter of the hollow interior 16 and the wall thickness of the probe increase in the downstream direction. The diameter of the hollow interior 16 increases up to some maximum diameter at a cross section 23 which may or may not coincide with the cross section at which the wall thickness is maximum. The hollow interior 16 of the probe 1 is connected to a conduit 14 by which material entering the probe 1 is fed to an analytical device (not shown). The analytical device may consist of a filter or other collector, a fractionator, a particle counter, or other means known in this art to qualitatively or quantitatively analyze the sample being gathered.

The probe 1 is located concentrically within a hollow cylindrical shroud 2. The shroud 2 is open to flow at an entry end 10 and an exhaust end 4 and together with the probe forms a restricted flow path at an annulus 6.

Figure 3:
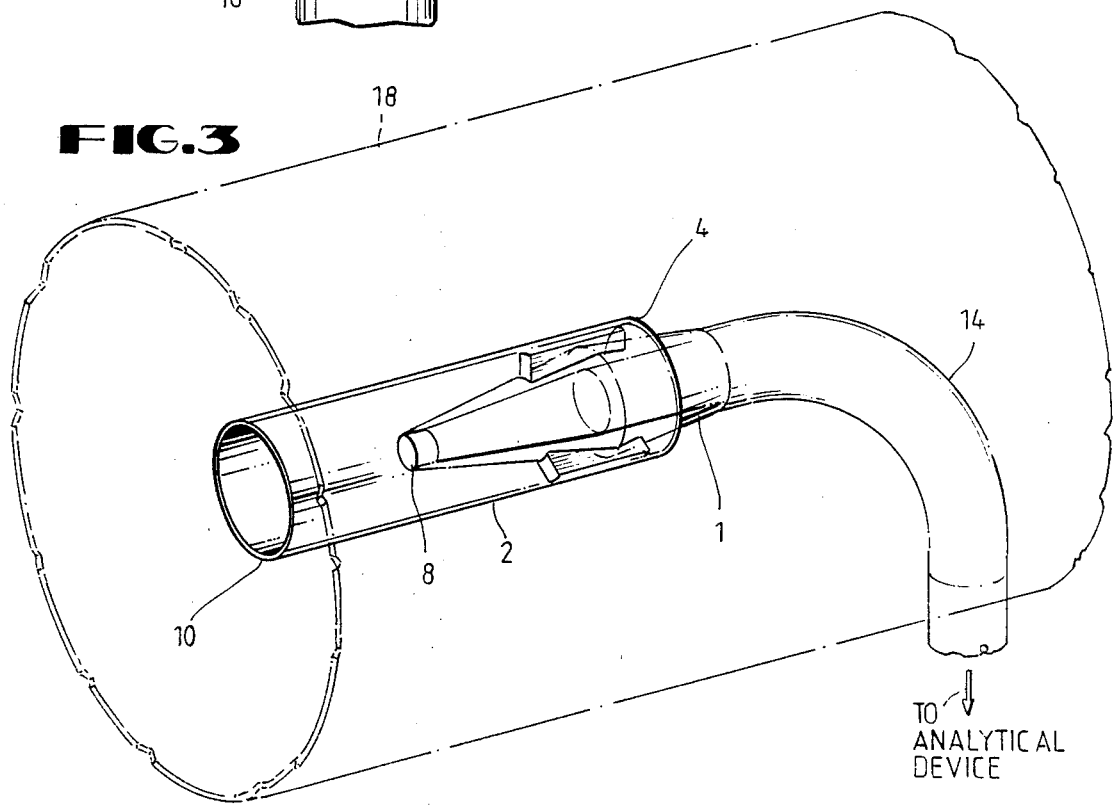
FIG. 3 is a partial cut-away perspective view of a shrouded probe as it would be installed in an air duct.

Referring also now to FIG. 3, we see how, in operation, an embodiment of the invented device may be located in an air duct 18. Alternatively, it may be located in any stream of fluid which is to be analyzed. The shrouded probe 1 is located so that its long axis is essentially parallel to the anticipated mean flow velocity vector U of the stream to be analyzed. (The angle of attack shown is 0 degrees but experiments were conducted with angles of attack up to 20 degrees.) The shroud entry end 10 and probe mouth 8 face into the flow stream 20 and the shroud exhaust end 4 faces downstream.

Now referring to FIG. 4, it can be seen that as a fluid is caused to flow past the shrouded probe 1, the fluid stream encounters the shroud entry end 10 before the probe mouth 8. The fluid streamlines tend to remain relatively straight; however, fluid which would enter the shroud 2 if all streamlines remained straight is diverted because the fluid velocity W just inside the shroud 2 is less than the mean velocity U of the free stream 20 fluid surrounding the shroud 2.

This deceleration of fluid entering the shroud 2 is caused by the restricted flow path through the annulus 6 formed between the interior 7 of the shroud 2 and the exterior 9 of the probe 1. All of the fluid entering the shroud entry end 10 must either enter the probe 1 or pass through the restricted flow area of the annulus 6 and then out of the probe exhaust 4 back into the free stream. The amount of restriction of the flow area determines the velocity W of the fluid inside the shroud 2 at the probe mouth 8. The shroud 2 acts as an aerodynamic decelerator. The annulus 6 between the shroud interior 7 and the thickest section of the probe body 12 restricts the fluid flow at that point. This causes the velocity W of the fluid just after entering the shroud 2 to be lower than the free stream velocity U.

Experimentation has shown that the ratio of free stream velocity to shroud velocity (U/W) remains essentially constant for a given shroud-probe configuration. The constancy of U/W means the shroud 2 can be designed to provide a fixed degree of deceleration to the fluid stream 20. One prototype probe was designed such that W/V=0.34. Thus, for a free stream velocity of 5 meters per second, the velocity in the annulus 6 would also be approximately 5 meters per se but the velocity W just inside the shroud inlet 10 would be 1.7 meters per second. Since the probe 1 is located inside the shroud 2 it "sees" only the much lower velocity W in the shroud. This allows the use of a physically larger probe 1 to take a given volume of sample fluid. Because the fluid velocity W in the shroud 2 is approximately one third of the free stream velocity U, a probe operating inside the shroud 2 can have a mouth area of three times that of a probe operating in the free stream and still operate isokinetically with the fluid surrounding it.

Reduction of fluid velocity is desirable because it will cause a reduction in wall loss effects and in losses or enrichment due to general anisokinetic effects. Because the predicted diameter of a probe will increase as the fluid velocity is decreased, for isokinetic operation at a fixed flow rate a lower velocity will permit the use of a larger diameter probe. In turn, the wall loss effects will be reduced because the ratio of particle stopping distance to the diameter of the probe mouth 8 is decreased. Also, the tendency for inertial enrichment or depletion in a probe is reduced as the stream velocity in the vicinity of the probe is decreased. The use of the shroud 2 also tends to cause the velocity vectors W to be more aligned with the axis of the probe 1 when there are non-zero angles of attack between the vectors U and V. The straightening effect of the shroud 2 also reduces turbulence in the fluid entering the probe 1 and the reduced turbulence tends to cause less particulate matter to be driven to the probe walls 22.

Comparison tests have been conducted with shrouded and unshrouded probes to determine the relative wall losses. In these tests, 10 micrometer diameter aerosol particles were introduced into a wind tunnel at a constant concentration. The fluid in the tunnel was then alternately sampled with a classic unshrouded isokinetic probe and with a shrouded probe operated at a fixed aspiration flow rate through the probe of 170 liters per minute. The particles contained an analytical tracer which was extracted in the laboratory by washing the internal surfaces of both probes with alcohol. Also each probe was fitted with a downstream filter to collect aerosol which was ingested into the probe inlet but not deposited on the walls. At a wind speed of 14 meters per second, the internal wall losses of the unshrouded isokinetic probe were 34%, whereas those of the shrouded probe were 10%. A comparison of various probe styles, wind speeds and angles of attack is shown below.

TABLE I

Wall Losses In Sampling Probes
Particle size = 10 μm aerodynamic diameter
Flow rate through probe = 170 L/min.

| Probe Type | Wind Speed | Angle of Attack | Wall Losses |
| --- | --- | --- | --- |
| Isokinetic/7° Taper | 14 m/s | 0 | 34% |
| Isokinetic/12° Taper | 14 m/s | 0° | 32 |
| Isokinetic/10° Taper | 7 | 0° | 18 |
| Shrouded Probe | 14 m/s | 0° | 10 |
|  |  | 20° | 13 |
|  | 7 | 0° | 5.3 |
|  | 4 |  | 4.6 |
|  | 2 |  | 5.6 |
| Probe Without Shroud Operated Isokinetically | 4 | 0° | 7.5 |

In addition to the wall loss effect improvements cited above, the general anisokinetic effects of probes operated in fluid streams are known to be approximately inversely proportional to the cube of the probe diameter. By increasing the probe diameter by a factor of 1.6, anisokinetic effects associated with the probe are reduced by a factor of approximately 4.

Again referring to FIG. 4, it can be seen that the shroud acts to force the streamlines 20 inside the shroud 2 to remain relatively straight in the vicinity of probe inlet 8. Smoke experiments in a wind tunnel with clear shrouds have verified that the streamlines remain relatively straight regardless of whether or not the probe 1 is operated isokinetically with the fluid inside the shroud 2. The effects shown in FIGS. 5b and 5c due to anisokinetic operation of the probe in a free stream are thereby reduced. Any deflection of the gas stream 20 and the resulting enrichment or depletion effects occur more at the outside region of the inside diameter of the entry end 10 of the shroud 2 rather than at the mouth 8 of the probe 1. If the shroud diameter is relatively large in relation to the probe diameter, the flow near the center of the shroud will enter the probe relatively undisturbed. The experiments conducted by the inventor used a 4-inch diameter shroud 2 surrounding a probe 1 having a 1-inch diameter mouth 8.

In order to determine the effectiveness of a shroud to reduce anisokinetic effects at the probe mouth, additional tests were conducted in an aerosol wind tunnel. Aerosol particles 10 micrometers in diameter were again released in known concentrations in the wind tunnel. The wind speed was varied from 2 meters per second to 7 meters per second and samples were taken alternatively with a shrouded probe and with a classic unshrouded probe. The shrouded probe, even though operated anisokinetically, produced a concentration ratio of 1.01 over the entire test range of wind speeds. The concentration ratio is based upon comparing the aerosol concentration downstream of cross section 23 with the total aerosol transmitted through and collected on the internal walls of the isokinetic probe. It is thus seen that use of the shrouded probe produced an insignificant error. Tests were also conducted to determine the effects of angle of attack between the vectors U and V. At a wind speed of 14 m/s, with 170 L/min of flow being drawn into the probe, the wall losses for 10 micrometer particles only varied from 10% to 13% as the angle of attack was changed from 0° to 20°.

The detailed description and experimental results appearing above are given for the purpose of disclosing preferred embodiments of the invention. Many modifications and variations to the apparatus described above will be obvious to one skilled in this art and may be made without departing substantially from the present invention. Accordingly, the preceding specification is exemplary only and is not intended to limit the scope of the present invention.

What is claimed is:

1. A method of taking samples from a flowing stream of fluid for analyzing the concentration of particulate matter in said flowing stream, comprising the steps of:

a. aerodynamically decelerating a portion of said flowing stream;

b. anisokinetically removing a sample of the decelerated fluid; and, c. analyzing the sample to determine the concentration of particulate matter contained therein.

2. The method of claim 1 wherein step (b) is performed by probe and step (a) is performed by a hollow shroud surrounding the probe.

3. The method of claim 2, wherein the mean velocity of the decelerated portion of the fluid stream is in the range of one fifth to four fifths of the mean velocity of the flowing stream.

4. The method of claim 2, wherein the mean velocity of the decelerated portion of the fluid stream is in the range of one quarter to three quarters of the mean velocity of the flowing stream.

5. The method of claim 2, wherein the mean velocity of the decelerated portion of the fluid stream is approximately one third of the mean velocity of the flowing stream.

6. A device for extracting a sample from a flowing fluid stream for analyzing the concentration of particulate matter in said sample which comprises:

a hollow probe located in the flowing fluid stream with a mouth end facing into the fluid flow to receive fluid, the probe being adapted to operate anisokinetically with the flowing fluid stream;

a shroud surrounding the mouth end of the probe, the shroud open at an entrance end to receive fluid flow and open at an exit end to discharge fluid flow; and, means connected to the probe for analyzing the fluid sample entering the probe.

7. The device of claim 6, wherein the flowing fluid has a mean velocity and the shroud in combination with the probe forms an aerodynamic restriction adapted to decelerate the mean velocity of the flowing fluid to a lower velocity at the mouth end of the probe.

8. The device of claim 6, wherein the ratio of the lower fluid velocity at the mouth of the probe to the flowing fluid velocity is in the range of 0.20 to 0.80.

9. The device of claim 6, wherein the probe and the shroud are sized relative to each other to achieve ratio of the lower fluid velocity at the open mouth of the probe to the flowing fluid velocity of 0.30 to 0.40.

10. The device of claim 6, wherein the probe and the shroud are sized relative to each other to achieve ratio of the lower fluid velocity at the open mouth of the probe to the flowing fluid velocity of approximately one third.

* * * * *

UNITED STATES PATENT AND TRADEMARK OFFICE
CERTIFICATE OF CORRECTION

PATENT NO. : 4,942,774

DATED : July 24, 1990

INVENTOR(S) : Andrew R. MacFarland

It is certified that error appears in the above-identified patent and that said Letters Patent is hereby corrected as shown below:

In Col. 2, line 5, please delete "less" (first instance) and insert --more--.

In Col. 5, line 54, please delete "se" and insert --second--.

Signed and Sealed this

Thirtieth Day of June, 1992

*Attest:*

DOUGLAS B. COMER

*Attesting Officer*  *Acting Commissioner of Patents and Trademarks*